United States Patent [19]

Richter et al.

[11] Patent Number: 5,770,619

[45] Date of Patent: *Jun. 23, 1998

[54] METHOD OF ACTIVATING PHOTOSENSITIVE AGENTS

[75] Inventors: Anna M. Richter; Elizabeth Waterfield; Julia G. Levy, all of Vancouver, Canada

[73] Assignee: University of British Columbia, Vancouver, Canada

[*] Notice: The term of this patent shall not extend beyond the expiration date of Pat. No. 5,705,518.

[21] Appl. No.: 551,471

[22] Filed: Nov. 1, 1995

Related U.S. Application Data

[63] Continuation of Ser. No. 391,414, Feb. 16, 1995, which is a continuation of Ser. No. 979,546, Nov. 20, 1992, abandoned.

[51] Int. Cl.$^6$ .................................................. A61K 31/41
[52] U.S. Cl. .......................... 514/410; 514/185; 514/253; 514/455; 514/561
[58] Field of Search ..................... 514/185, 253, 514/410, 455, 561; 540/145

[56] References Cited

U.S. PATENT DOCUMENTS

| | | | |
|---|---|---|---|
| 4,521,762 | 6/1985 | Kapral | 341/122 |
| 4,577,636 | 3/1986 | Spears | 128/654 |
| 4,753,958 | 6/1988 | Weinstein et al. | 514/410 |
| 4,866,168 | 9/1989 | Dougherty et al. | 540/145 |
| 4,878,891 | 11/1989 | Judy et al. | 604/5 |
| 4,925,736 | 5/1990 | Shikowitz | 424/449 |
| 4,935,498 | 6/1990 | Sessler et al. | 534/15 |
| 4,957,481 | 9/1990 | Gatenby | 604/20 |
| 4,973,848 | 11/1990 | Kolobanov et al. | 250/458.1 |
| 5,028,594 | 7/1991 | Carson | 514/23 |
| 5,095,030 | 3/1992 | Levy et al. | 514/410 |
| 5,484,803 | 1/1996 | Richter | 514/410 |

FOREIGN PATENT DOCUMENTS

| | | |
|---|---|---|
| 2012175 | 3/1990 | Canada . |
| 337 601 | 10/1989 | European Pat. Off. . |
| 478 506 | 4/1992 | European Pat. Off. . |
| WO 90/11797 | 10/1990 | WIPO . |

OTHER PUBLICATIONS

Jamieson et al., Leukemia Research, vol. 14, No. 3, pp. 209–219, 1990.

Richter et al., Biochemical Pharmacology, vol. 43, No. 11, pp. 2349–2358, 1992.

Kostron et al., "Photodynamic therapy is potentiated by $Co^{80}$ and intratumoral injection of hematoporphyrin derivative" *J. Neuro–Oncology* (1988) 6:185–191.

Dougherty et al., "Cutaneous phototoxic occurrences in patients receiving photofrin" *Lasers in Surgery and Medicine* (1990) 10:485–488.

Harty et al., "Complications of whole bladder dihematoporphyrin ether photodynamic therapy" *J. Urology* (1989) 141:1341–1346.

Cohen et al., "Modification of radiosensitivity by porphyrins II. transplanted rhabdomyosarcoma in mice" *Cancer Res.* (1966) 25:1769–1773.

Doss, M., Ed., *Diagnosis and Therapy of Porphyrias and Lead Intoxication* (1978) Springer–Verlag, Berlin, Germany, pp. 229–235.

*Primary Examiner*—Richard L. Raymond
*Attorney, Agent, or Firm*—Morrison & Foerster LLP

[57] ABSTRACT

A method of administering photodynamic therapy begins with administering to an animal an effective amount of a photosensitizing agent which is less than about one half of the usual clinical dose for the photosensitizing agent. Then, following a post injection interval which is less about one quarter of the usual post injection interval, an effective dose of light which is less than about one half of the usual clinical dose of light used in conjunction with the photosensitizing agent is administered to the animal.

13 Claims, 2 Drawing Sheets

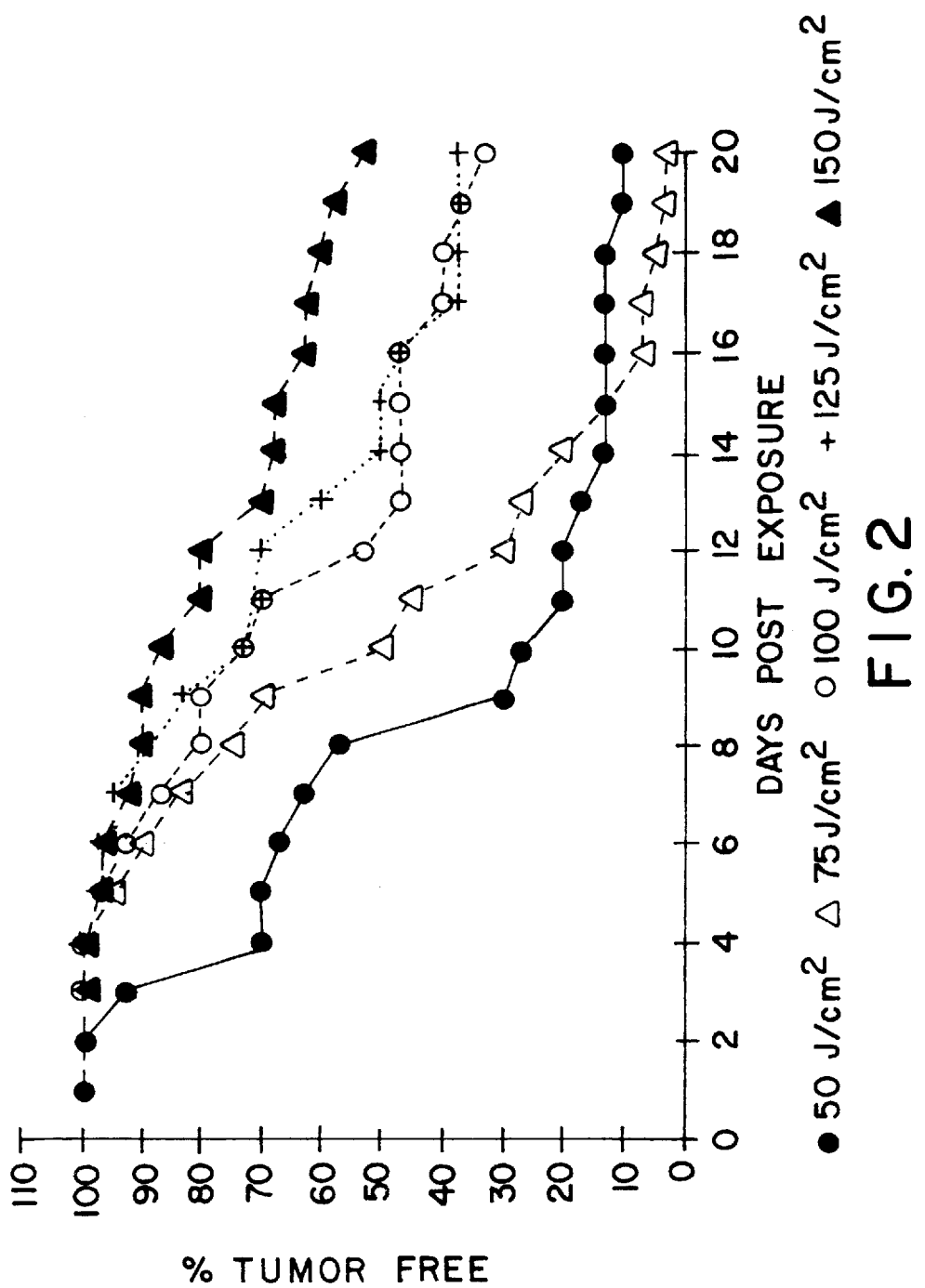

METHOD OF ACTIVATING PHOTOSENSITIVE AGENTS

This application is a continuation of application Ser. No. 08/391,414, filed Feb. 16, 1995, which is a continuation of application Ser. No. 07/979,546, filed Nov. 20, 1992, now abandoned.

FIELD OF THE INVENTION

This invention relates generally to the field of medicine and pharmacotherapeutics with photosensitizing agents. Specifically, the invention is a method of destroying target tissue which entails administration of a photosensitizing agent and application of radiation to selectively impair or destroy the target tissue.

BACKGROUND OF THE INVENTION

Photodynamic therapy (PDT) involves the administration of a photosensitizing compound and subsequent irradiation with light of tissue in which the photosensitizing compound has concentrated. Target tissue containing a sufficiently high concentration of the photosensitizing compound selectively absorbs the light which induces impairment or destruction of the immediately surrounding cells. U.S. Pat. No. 5,095,030 issued to Levy on 10 Mar. 1992 describes procedures for administering photosensitizing compounds to animals which are subsequently irradiated using external light sources. For example, Example 5 of this patent describes subcutaneous injection of mice with P815 tumor cells which grow into a palpable tumor. Photosensitizing compounds are then injected. Then the animals are maintained in the dark for two hours. Next, their tumors were exposed to a strong light. The survival rates of the treated animals were significantly improved over untreated controls. Similarly, Example 8 of that patent describes use of a rhabdomyosarcoma system in mice with a similar protocol. However, in this case light exposure commenced 24 hours post injection. In addition, biodistribution of tritiated BPD-MA and BPD-MB was determined post injection at times ranging from 3–168 hours. Tumor-skin ratios were favorable three hours after IV administration. Biodegradability was determined with tritiated BPD-MA injected IV into P815 tumor-bearing mice. Mice were sacrificed at three or 24 hours after BPD-MA injection; and tumors, livers and kidneys were evaluated. After 3 hours 100% of BPD-MA in the tumor was active, but only 39% was active at 24 hours. Both livers and kidneys degraded BPD-MA more quickly than did the tumors.

Kostron et al. (*J. Neuro-Oncology* (1988) 6:185–91) injected hematoporphyrin derivative directly into subcutaneous rat gliosarcomas and irradiated 48 hours post injection. Kostron reported that direct injection appeared to be safer than parenteral injection. Kostron also mentioned previous studies indicating that there should be a post injection delay of at least two days and preferably three to four days before light was applied because that would permit the hematoporphyrin derivative to concentrate in tumor cells.

BPD also has demonstrated a higher affinity for tumor tissue, including leukemic cells, than for normal non-malignant cells. Jamieson et al., *Leukemia Res.* 14:209–19, 1990. Photosensitizers also are useful in the detection and treatment of atherosclerotic plaque as described in U.S. Pat. Nos. 4,521,762 and 4,577,636. The treatment of viral diseases is disclosed in U.S. Pat. No. 4,878,891, issued 7 Nov. 1989 to Judy et al.; U.S. Pat No. 4,925,736, issued 15 May 1990 to Shikowitz; and U.S. Pat. No. 4,935,498. Psoriasis treatment is disclosed in U.S. Pat. No. 4,753,958, issued 28 Jun. 1988 to Weinstein et al. Arthritis treatment is disclosed in U.S. Pat. No. 5,028,594, issued 2 Jul. 1991 to Carson. Portwine stain treatment is disclosed in Canadian patent publication CA 2,012,175.

U.S. Pat. No. 5,095,030, issued 10 Mar. 1992, which is incorporated herein in its entirety by reference, discloses and claims various wavelength-specific cytotoxic agents which are generically described as "green porphyrins." These compounds are porphyrin derivatives which are modified by a Diels-Alder reaction effectively to shift the wavelength of absorption to a longer wavelength. This results in some favorable properties as compared to, for example, hematoporphyrin derivative when these compounds are employed in photodynamic therapy generally. As described in this patent, these cytotoxic agents, when administered systemically, "home" to unwanted cells, in particular to tumor cells or viruses. Subsequent irradiation with light absorbed by these compounds is cytotoxic.

Pending application Ser. No. 07/832,542, filed Feb. 5, 1992, now abandoned and refiled as Ser. No. 08/489,850, which is incorporated herein in its entirety by reference, discloses the preparation of liposomes of porphyrin photosensitizers.

Pending application Ser. No. 07/948,113, now abandoned and refiled as Ser. No. 08/384,440, now U.S. Pat. No. 5,484,803 which is incorporated herein in its entirety by reference, discloses the injection of BPD into mice to treat blood-borne target cells. This application also discloses pharmacokinetic data at post injection intervals between 15 minutes and two hours. All mice given doses of 6.32 $\mu$g/ml and illuminated starting at 15 minutes post injection died. However, other mice injected with lower BPD doses or longer post injection times (e.g., one hour) remained healthy.

Adverse effects following the administration of PROTOFRIN® porfimer sodium have been documented by Dougherty et al. *Lasers in Surg. Med.* (1990) 10:485–88; and Harty et al. *J. Urology* (1989) 141:1341–46. In a series of 180 patients treated with porfimer sodium, Dougherty reported that patients received 0.5 to 2.0 mg/kg to treat a variety of cancers but did not mention light dose or post injection interval before light treatment. However, the recommended post injection interval for this drug is 24–48 hours. Dougherty cautions that "all patients are photosensitive following injection of Photofrin." Treated patients were polled in person and through questionnaires about photosensitivity reactions. The in-person reports of reactions were believed to be uncommonly low, as patients may have avoided admitting violating medical instructions to avoid sunlight for a month. Nevertheless, nearly a quarter of the patients reported reactions, most of which occurred within one month of the treatment. There was "no apparent relationship of photosensitivity to injected drug dose . . . although there may be a trend to less severe reactions at the lower drug doses." In addition, the length of time to lose photosensitivity may have been somewhat shorter for the 5 mg/kg group, but it was not statistically significant. Dougherty concludes that patients should be warned that photosensitivity may last six weeks.

Harty et al. treated 7 patients with bladder cancer with an intravenous injection of 2.0 mg/kg of PHOTOFRIN porfimer sodium (one patient received $\frac{2}{3}$ of the proper dose), followed 72 hours later by exposure to energy density of 100 J/cm$^2$. "Six patients had skin phototoxicity and in each case this occurred within 10 days after administration of [the drug]. Four cases were classified as mild, consisting of erythema and edema of the hands and face and did not require treatment. In 2 patients the phototoxicity was of moderate severity, consisting of second degree burns of hands and face, and required topical therapy." Five patients had irritative bladder symptoms which were associated with loss of smooth muscle and its replacement by fibrous tissue.

What is needed is a better method to administer photodynamic therapy to avoid adverse side effects such as normal tissue destruction and photosensitivity reactions. An improved method of therapy also would use a lower light dose, so that treatment could be administered more quickly and efficiently. When the light source emits at a limited power, an improved method would permit shorter light treatment periods and more patients to be treated with the same light source. Another improvement would be a lower dose of the photosensitizing agent, which would lower the cost of treatment and also help avoid side effects.

SUMMARY OF THE INVENTION

This invention provides a method of administering photodynamic therapy to an animal. The method has two steps: First, an effective amount of a photosensitizing agent is administered to the animal. The effective amount of the photosensitizing agent in this method is less than about one half of the usual clinical dose for the same photosensitizing agent. Second, after a post injection interval of less than about one fourth the usual interval, an effective dose of light is administered to the animal. The effective dose of light is less than about one half of the usual clinical dose of light used in conjunction with the particular photosensitizing agent.

In another embodiment, the invention is applied to targets which include, but are not limited to, tumors, atherosclerotic plaque, localized viral infections, psoriasis, arthritic joints, and ocular and other neovascularization or hypervascularizations.

While this invention provides for the use of any photosensitizing agent, preferably the agent is selected from chlorins (such as chlorin e6), bacteriochlorins, phthalocyanines, porphyrins, purpurins, merocyanines, pheophorbides, psoralens, and pro-drugs such as δ-aminolevulinic acid which can produce drugs such as protoporphyrin in tissue. In other embodiments, BPD-MA, monoaspartyl chlorin e6, zinc phthalocyanine, tin etiopurpurin, tetrahydroxy tetraphenylporphyrin, and porfimer sodium are the photosensitizing agents.

In another embodiment, there is provided a two-step method for administering photodynamic therapy to an animal. First, a photosensitizing agent is administered to an animal in an amount sufficient to produce a photodynamic effect. Second, after a post injection interval of less than about two hours, less than about 75 Joules/cm$^2$ of light is administered to the animal.

BRIEF DESCRIPTION OF THE DRAWINGS

FIG. 2 is a graph showing the light dose response curve for doses of 50, 75, 100, 125 and 150 J/cm$^2$. Light exposure took place three hours after the injection of 2 mg/kg BPD-MA.

BRIEF DESCRIPTION OF THE INVENTION

Figure 1:
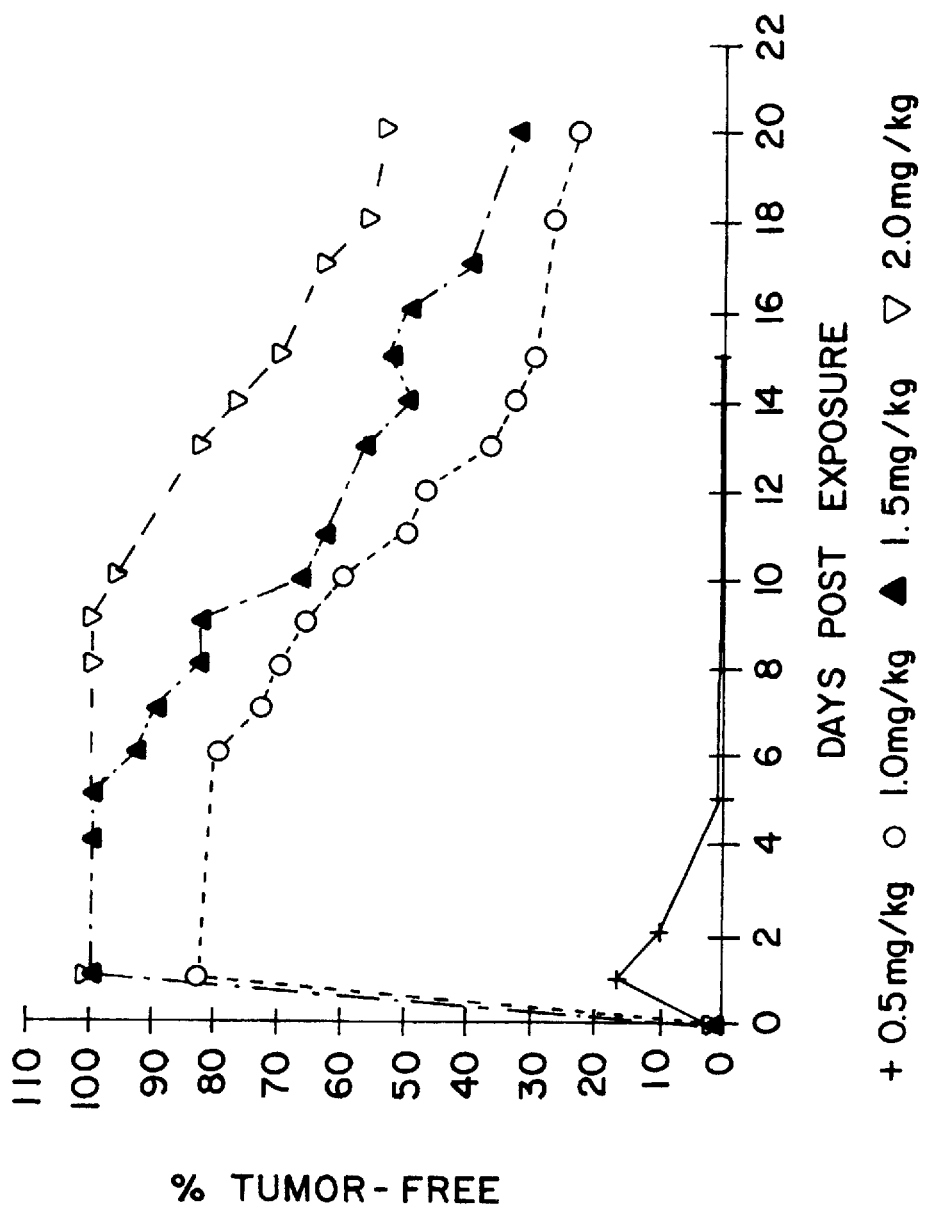
FIG. 1 is a graph showing the BPD-MA dose response curve for doses of 0.5, 1.0, 1.5 and 2.0 mg/kg. Light exposure took place three hours after injection.

This invention is a method of administering photodynamic therapy. The method comprises administering a photosensitizing agent and applying radiation to at least a portion of an intact animal at an intensity effective to impair or destroy selectively target tissue.

As used herein "target" is that tissue that is intended to be impaired or destroyed by this treatment method. The target takes up the photosensitizing agent; then when sufficient radiation is applied, the target tissue is impaired or destroyed. Targets include, but are not limited to, tumors, atherosclerotic deposits, virus-containing cells such as those infected with papillomavirus (warts), psoriasis, and arthritis. Also included among target cells are rapidly developing capillaries and areas of neovascularization, particularly in the eye. This improved method can be used with the types of tumors with which photodynamic therapy has been used in the past. These tumors generally are rather shallowly located on the body through which the light must penetrate. These include various tumors of the skin, bladder and neck, Kaposi's sarcoma and some esophageal tumors.

"Non-target cells" are all the cells of an intact animal which are not intended to be impaired or destroyed by the treatment method. These non-target cells include but are not limited to those of other healthy tissues, including overlying normal skin.

"Destroy" is used to mean kill the desired target tissue. "Impair" means to change the target tissue in such a way as to interfere with its function. For example, North et al. observed that after exposure of BPD-treated, virus-infected T cells to light, holes developed in the T cell membrane, which increased in size until the membrane completely decomposed (*Blood Cells* 18:129–40, 1992). Target tissues are understood to be impaired or destroyed even if the target cells are ultimately disposed of by macrophages.

"Photosensitizing agent" is a chemical compound which homes to one or more types of selected target tissues and, when contacted by radiation, absorbs the light and induces impairment or destruction of the target tissues. Virtually any chemical compound that homes to a selected target and absorbs light may be used in this invention. Preferably, the chemical compound is nontoxic to the animal to which it is administered or is capable of being formulated in a nontoxic composition. Preferably, the chemical compound in its photodegraded form is also nontoxic. A comprehensive listing of photosensitive chemicals may be found in Kreimer-Birnbaum, *Sem. Hematol.* 26:157–73, 1989. Photosensitive compounds include, but are not limited to, chlorins, bacteriochlorins, phthalocyanines, porphyrins, purpurins, merocyanines, pheophorbides, psoralens and pro-drugs such as δ-aminolevulinic acid, which can produce drugs such as protoporphyrin. A new class of photosensitizing agents, wavelength-specific photosensitive porphacyanine and expanded porphyrin-like compounds is disclosed in U.S. Pat. No. 5,405,957, and incorporated herein in its entirety by reference, can be used in the disclosed method. Preferred photosensitizing agents are benzoporphyrin derivatives (BPD), monoaspartyl chlorin e6, zinc phthalocyanine, tin etiopurpurin, tetrahydroxy tetraphenylporphyrin and porfimer sodium (PHOTOFRIN®). Most preferred is the benzoporphyrin derivative monoacid ring A (BPD-MA).

"Radiation" or "light" as used herein includes all wavelengths. Preferably, the radiation wavelength is selected to match the wavelength(s) which excite(s) the photosensitive compound. Even more preferably, the radiation wavelength matches the excitation wavelength of the photosensitive compound and has low absorption by the non-target tissues and the rest of the intact animal. For example, the preferred wavelength for BPD-MA is the range of 685–695 nm. A preferred light source is an argon pumped dye laser which is tuned to emit at about 690 nm. Also useful are fluorescent banks of lights, LED panels, and filtered full spectrum arc lamps.

The radiation is further defined in this invention by its intensity, duration, and timing with respect to dosing with the photosensitive agent (post injection interval). The intensity must be sufficient for the radiation to penetrate skin and/or to reach the target tissues to be treated. The duration must be sufficient to photoactivate enough photosensitive agent to act on the target tissues. Both intensity and duration must be limited to avoid overtreating the animal. The post injection interval before light application is important, because in general the sooner light is applied after the photosensitive agent is administered, 1) the lower is the required amount of light and 2) the lower is the effective amount of photosensitive agent.

This invention provides a method of treating an animal, which includes, but is not limited to, humans and other mammals. The term "mammals" also includes farm animals, such as cows, hogs and sheep, as well as pet or sport animals such as horses, dogs and cats.

By "intact animal" is meant that the whole, undivided animal is available to be exposed to light. No part of the animal is removed for light treatment, in contrast with photophoresis, in which the animal's blood is circulated outside its body for exposure to light. The entire animal need not be exposed to light. Only a portion of the intact animal may or need be exposed to radiation. For discrete tumors and other conditions affecting a relatively small volume, it is preferable to apply light solely to the skin overlying the tumor or other condition.

"Transcutaneously" is used herein as meaning through the skin of an animal.

Typical indications for this treatment include destruction of tumor tissue in solid tumors, dissolution of atherosclerotic plaque in blood vessels, treatment of topical tumors or skin disease including papillomavirus infections (e.g., warts), psoriasis, arthritis, and conditions characterized by neovascularization or hypervascularization, particular of the eyes.

Briefly, the photosensitizing agent is generally administered to the animal before the animal is subjected to light treatment. Preferably, the agent is administered at a post injection interval which is less than one quarter of the usual post injection interval before subjecting the animal to light treatment.

Preferred photosensitizing agents include, but are not limited to, chlorins, bacteriochlorins, phthalocyanines, porphyrins, purpurins, merocyanines, pheophorbides, psoralens and pro-drugs such as δ-aminolevulinic acid, which can produce drugs such as protoporphyrin. More preferred are benzoporphyrin derivatives (BPD) and porfimer sodium. Most preferred among the benzoporphyrin derivatives is the monoacid ring A (BPD-MA). Other preferred photosensitizing agents include but are not limited to monoaspartyl chlorin e6, zinc phthalocyanine, tin etiopurpurin and tetrahydroxy tetraphenylporphyrin.

The photosensitizing agent is administered locally or systemically. The photosensitizing agent is administered gastrointestinally or by injection which may be intravenous, subcutaneous, intramuscular or intraperitoneal. The photosensitizing agent also can be administered enterally or topically via patches or implants. The most preferred method of administration is intravenous injection.

The photosensitizing agent can be synthesized as a dimer and thereby absorb more light on a per mole basis.

The photosensitizing agent can be administered in a dry formulation, such as pills, capsules, suppositories or patches. The photosensitizing agent also may be administered in a liquid formulation, either alone with water, or with pharmaceutically acceptable excipients, such as are disclosed in *Remington's Pharmaceutical Sciences*. The liquid formulation also can be a suspension or an emulsion. In particular, liposomal or lipophilic formulations are most preferred. If suspensions or emulsions are utilized, suitable excipients include water, saline, dextrose, glycerol, and the like. These compositions may contain minor amounts of nontoxic auxiliary substances such as wetting or emulsifying agents, antioxidants, pH buffering agents, and the like.

The dose of photosensitizing agent will vary with the target cell(s) sought, the animal's weight and the timing of the light treatment. For known photosensitizing agents, the effective amount of the photosensitizing agent needed in this method is approximately less than half of the known usual clinical dose. For example, the usual clinical dose is 2.5 mg/kg for porfimer sodium and 0.25 mg/kg for BPD. The effective amount of porfimer sodium in this method is about 0.3 to 1.25 mg/kg. The effective amount of BPD in this method is about 0.01 to 0.125 mg/kg. The usual clinical doses for monoaspartyl chlorin e6 (0.1–2.5 mg/kg), zinc phthalocyanine (0.5–2 mg/kg), tin etiopurpurin (0.5–2 mg/kg) and tetrahydroxy tetraphenylporphyrin (1–5 mg/kg) are halved for use in this method.

The dose of light administered also is much lower in this method than in known methods for photodynamic therapy. In general, the light dose is less than about half of the light dose of previous methods. For example, where previously 150 Joules/cm$^2$ was used with BPD, the method of the present invention requires no more than 75 Joules/cm$^2$. Where previously 10–50 Joules/cm$^2$ was used with monoaspartyl chlorin e6, the method of the present invention requires no more than about half of the previous light doses.

The duration of radiation exposure is preferably between about 5 and 30 minutes, depending on the power of the radiation source.

The post injection interval in this method varies by the photosensitizing agent. However, the post injection interval in one embodiment is less than about one fourth the clinical post injection interval used with known photosensitizing agents. For example, the usual clinical post injection interval for BPD is about 3 hours. In contrast, the post injection interval for BPD in this invention is less than about one quarter of that, or less than about 45 minutes. The usual clinical post injection interval for porfimer sodium is 24–48 hours. In contrast, the post injection interval in this invention is less than about 6 hours for porfimer sodium, and preferably less than about 4 hours.

This invention is the conduct of effective PDT more safely and with fewer adverse effects because the post injection interval is much shorter and doses of both the photosensitive agent and light are halved. In contrast, previously it was thought that the photosensitizer initially distributed nonselectively throughout the body and that it took several hours to days for the photosensitizer to accumulate selectively in the target tissue. It was thought that selective distribution occurred gradually, with a considerable amount of exchange between the target tissue and the pool of circulating photosensitizer molecules. Thus, it was considered essential to delay post injection light treatment by several hours to days.

However, a recent pharmacokinetic study has brought this long-accepted thinking into question. Richter et al. (*Biochem. Pharmacol.* (1992) 43:2349–58) reported that administered BPD has two regioisomers in equal concentrations. By 3 hours post injection, the isomer ratio in plasma changes from about 1:1 to 1:0.28, due to liver metabolism. However, when tumor tissue was removed 15 min and three hours post injection, and BPD extracted from it, the isomers were found at essentially equal proportions (1:1.15).

While not wishing to be limited by a theory, the inventors propose these data suggest the possibility that BPD may accumulate rapidly in tumors, where it may be immobilized, and permit shorter post injection intervals.

Previously it was assumed that after injection, photosensitizers first distributed equally to target and normal tissues. This was the basis for the assumption that a short post injection interval would cause extensive damage to normal tissue, particularly skin.

Yet as disclosed in Example 3 of U.S. application Ser. No. 948,113, abandoned and refiled as Ser. No. 08/384,440, now U.S. Pat. No. 5,484,803, mice injected with BPD can receive relatively high levels of light (about 150 J/cm$^2$) on their shaved backs without any apparent ill effects so long as exposure takes place within the first two hours post injection (as opposed to the usual three hours). Blood sampling of those treated animals indicates that almost 80% of circulating BPD becomes photobleached by this treatment indicating that light has activated the drug. Therefore, photosensitizers may not produce generalized tissue damage even when activated by light, so long as there is insufficient photosensitizer present in surrounding cells.

These two surprising results encouraged testing of early, lower dose illumination in tumor treatment with PDT (i.e., before photosensitizers permeate skin or other normal tissue). Experimental evidence (presented below) in mice indicates the inventive method is safe and effective.

The examples which follow are intended to demonstrate the efficacy of the invention and to assist in the practice of the invention. The following examples cover one photosensitizing agent and provide a means to screen other photosensitizing agents or new compounds for use in the inventive method. The following examples are intended only to be examples and not to limit the invention in any way.

General Comments

The following general comments on Materials and Procedures apply to Examples 1 and 2, unless otherwise noted.

BPD-MA was synthesized as described in U.S. Pat. Nos. 4,920,143 and 4,883,790, incorporated herein by reference. BPD-MA was obtained from QuadraLogic Technologies, Inc. and stored dissolved in DMSO (4.5 mg/ml) at −70° C. Liposomal BPD (4.95 mg/ml) was prepared as described in U.S. application Ser. No. 07/832,542, filed Feb. 5, 1992 now abandoned and refiled as 08/489,850. The following formula was used:

| Ingredient | Amount (mg/ml) |
|---|---|
| BPD-MA | 4.95 |
| Dimyristoyl Phosphatidyl Choline | 23.27 |
| Egg Phosphatidyl Glycerol | 16.09 |
| Lactose or Trehalose | 148.50 |
| Ascorbyl Palmitate | 0.05 |
| Butylated Hydroxy Toluene | 0.005 |
| Water for Injection | Q.S. |

Liposomal BPD was dried and stored frozen at −20° C. in 1 ml aliquots. The appropriate number of aliquots were thawed immediately before use and diluted with 5% dextrose in water for injection into the animals.

Male DBA/2 mice (7–11 weeks old; Charles River Laboratories, St. Constant, Quebec, Canada) were used in these studies, unless otherwise specified. Shaving and depilation removed the hair very effectively from appropriate body surfaces. The mice were shaved and depilated with a commercially available depilator (Nair®) at least one day before being used in the experiments. Following injection the mice were kept in the dark for various lengths of time, as described below. Before and after the experiments the mice were kept in an animal facility with 12 hours of light and 12 hours of dark daily.

An argon pumped dye laser, whose power source was obtained from SpectraPhysics (Series 2000, Mountain View, Calif.) and whose 5W argon ion pumped dye laser was obtained from Coherent (Model 599, Palo Alto, Calif.) was used to deliver a columnated beam of light having a wavelength of 690 (±3) nm. The argon laser was aimed at the skin to irradiate the tumor. The time of light exposure was varied to give different light doses, such as 50, 75 and 100 Joules/cm$^2$.

EXAMPLE 1

Pilot Study of Shorter Post Injection Intervals

DBA/2 mice (weight 22 ±1 g) were used in this study. First, mice were injected in the flank with M-1 (murine rhabdomyosarcoma) tumor cells and the tumors were allowed to grow to about 5 mm in diameter, according to the protocol of Richter et al., Br. J. Cancer (1991) 63:87–93. Mice were injected with liposomal BPD-MA and kept in the dark for 15 minutes before exposure to light. The mice were then treated with the laser.

At 48 hours after the mouse was treated with 1 mg/kg of BPD-MA and 100 J/cm$^2$ of light, the mouse was still alive and when viewed resting on its belly in profile, its back still appeared clean-shaven and displayed a large crescent-shaped eschar, which was about the size of its ear. This eschar was located on the mouse's flank where the tumor was eradicated. The tumor was not palpable.

At 24 hours after treatment with 0.5 mg/kg BPD-MA and 75 J/cm$^2$ light, the treated mouse was alive and when viewed resting on its belly in profile, its back still appeared clean-shaven and displayed a small, round inflamed, or darkly colored, area located on the mouse's flank where the tumor was eradicated. There was no eschar. The tumor was not palpable. FIG. 2 shows that after only 24 hours, the normal skin surrounding the tumor was only slightly inflamed.

Both animals were followed two weeks. The tumors did not grow back; and there was a flat, healing area of skin.

A mouse with an M-1 tumor was evaluated four days after treatment. The treatment differed somewhat from the two preceding regimens. This mouse was treated with 2.0 mg/kg of BPD-MA and irradiated with 100 Joules/cm$^2$ of light, administered three hours post injection. The mouse was alive and when viewed resting on its belly in profile, its back still appeared clean-shaven and displayed a large crescent-shaped eschar, which was about the size of its ear. This eschar was located on the mouse's flank where the tumor was eradicated. The tumor was not palpable.

A comparison of the mouse evaluated at 24 hours after treatment with 0–5 mg/kg BPD-MA and 75 J/cm$^2$ light with the mice either evaluated after 48 hours after treatment with 1 mg/kg BPD-MA and 100 J/cm² of light or evaluated four days after treatment with 2.0 mg/kg BPD-MA and 100 J/cm² of light, shows there is a reduction in skin damage when the post injection interval is shortened and when the doses of the BPD-MA and light are reduced.

EXAMPLE 2

Dose Ranging Study

Additional DBA/2 mice were prepared with M-1 tumor cells as described above. The tumors were allowed to grow to approximately 5 mm diameter. Then, the mice were injected with one of two different doses of BPD-MA (0.5 and 1.0 mg/kg), exposed to one of three different light doses (50, 75 and 100 J/cm²), and exposed to light at one of three different post injection intervals (1, 15 and 30 minutes). During the 15 and 30 minute post injection intervals, the mice were kept in darkness.

Table 1 shows the number of animals which were tumor free at each observation period for each drug and light dose and at each post injection interval. Many of the animals have recently started the test. Only a few animals were treated long enough ago to be followed to day 14. Of those, most are tumor free.

TABLE 1

Interim Test Results for Dose-Ranging Time-Varying Study

| Treatment | | | | | |
|---|---|---|---|---|---|
| Drug Dose (mg/kg) | Light Dose (J/cm²) | Time Post Injection (min.) | Results (# Tumor-Free) | | # of Mice |
| | | | Day 7 | Day 14 | |
| 0.5 | 50 | 1 | 3 | n/a | 3 |
| 0.5 | 50 | 15 | 2 | n/a | 2 |
| 0.5 | 50 | 30 | 0 | 0 | 2 |
| 0.5 | 75 | 1 | 2* | n/a | 2 |
| 0.5 | 75 | 15 | 2 | 2 | 2 |
| 0.5 | 75 | 30 | n/a | n/a | n/a |
| 0.5 | 100 | 1 | 3 | n/a | 3 |
| 0.5 | 100 | 15 | 5 | 2 | 5 |
| 0.5 | 100 | 30 | 2 | n/a | 2 |
| 1.0 | 50 | 1 | 4 | n/a | 4 |
| 1.0 | 50 | 15 | 4 | 4 | 4 |
| 1.0 | 50 | 30 | 4 | 4 | 5 |
| 1.0 | 75 | 15 | 5 | 4 | 5 |
| 1.0 | 75 | 30 | 4 | n/a | 5 |
| 1.0 | 100 | 15 | 4 | 4 | 4 |

NOTE:
(*): observations on Day 2 post exposure
n/a: animals have not been tested or animals have not been in study long enough to reach observation date At the 0.5 mg/kg BPD-MA dose and 50 J/cm² administered 30 minutes post injection, all mice developed tumors. Three of five mice given 0.5 mg/kg BPD-MA and 100 J/cm² administered 15 minutes post injection also developed tumors by day 14, although all were tumor free at day 7.

For comparison, FIGS. 1 and 2 are provided. FIG. 1 summarizes results of a test involving the same mouse-tumor model, in which four different BPD-MA doses were given (0.5, 1.0, 1.5, and 2.0 mg/kg). Light exposure was 150 J/cm², administered after a post injection interval of three hours of darkness. Under this regimen, which is similar to current clinical regimens, the only group that was over 50% tumor free at 14 days was that group of mice receiving 2.0 mg/kg. This dose was at least double the effective doses displayed in Table 1.

FIG. 2 summarizes results of a test involving the same mouse-tumor model, in which five different light exposures (50, 75, 100, 125 and 150 J/cm²) were used three hours post injection with 2 mg/kg BPD-MA. Under this regimen, which is similar to current clinical regimens, 75% of the mice receiving 150 J/cm² and 50% of the mice receiving 125 J/cm² were tumor free at 14 days. These doses of light were significantly higher than the lowest effective doses displayed in Table 1.

This invention has been described by a direct description and by examples. As noted above, the examples are meant to be only examples and not to limit the invention in any meaningful way. Additionally, one having ordinary skill in this art in reviewing the specification and claims which follow would appreciate that there are equivalents to those claimed aspects of the invention. The inventors intend to encompass those equivalents within the reasonable scope of the claimed invention.

We claim:

1. A method to destroy or impair an area of neovascularization in an animal, which animal comprises both an area of neovascularization and normal tissue, which method comprises:

(a) administering to said animal an effective amount of a photosensitizing agent;

(b) administering to said area of neovascularization an effective amount of light of a wavelength that matches an excitation wavelength of said photosensitizing agent, wherein said light is administered to said area of neovascularization before said photosensitizing agent has permeated said normal tissue.

2. The method of claim 1, wherein the time between step (a) and step (b) is less than one quarter of the clinical interval for subjecting the animal to light treatment after administering said photosensitizing agent.

3. The method of claim 1 wherein the effective amount of the photosensitizing agent is approximately less than one half of the clinical dose of said photosensitizing agent in photodynamic therapy.

4. The method of claim 1 wherein the effective amount of light is less than about half of the clinical dose of light for activation of the photosensitizing agent in photodynamic therapy.

5. The method of claim 1 herein the photosensitizing agent is selected from the group consisting of a chlorin, a bacteriochlorin, a phthalocyanine, a porphyrin, a purpurin, a merocyanine, a pheophorbide and a psoralen.

6. The method of claim 5 wherein said photosensitizer is a porphyrin.

7. The method of claim 6 wherein the porphyrin is BPD or porfimer sodium.

8. The method of claim 7 wherein the porphyrin is BPD-MA.

9. The method of claim 1 wherein the animal is mammal.

10. The method of claim 9 wherein the mammal is a human.

11. The method of claim 8 wherein the postinjection time varies between about one minute and 45 minutes.

12. A method to destroy or impair an area of neovascularization in an animal, which animal comprises both an area of neovascularization and normal tissue, which method comprises:
- (a) administering to said animal an effective amount of benzoporphyrin derivative-monoacid (BPD-MA); and
- (b) administering to said area of neovascularization an effective amount of light of a wavelength that matches an excitation wavelength of said BPD-MA, wherein said light is administered to said area of neovascularization before said BPD-MA has permeated said normal tissue;

and wherein the time between step (a) and (b) varies between about one minute and 45 minutes.

13. The method of claim 12 wherein said area of neovascularization is a solid tumor.

* * * * *